United States Patent
Soon-Shiong

(10) Patent No.: US 12,016,872 B2
(45) Date of Patent: *Jun. 25, 2024

(54) PATIENT TREATMENT VIA TERATOGENIC PHARMACEUTICAL COMPOUNDS

(71) Applicant: Nant Holdings IP, LLC, Culver City, CA (US)

(72) Inventor: Patrick Soon-Shiong, Culver City, CA (US)

(73) Assignee: Nant Holdings IP, LLC, Culver City, CA (US)

( * ) Notice: Subject to any disclaimer, the term of this patent is extended or adjusted under 35 U.S.C. 154(b) by 844 days.

This patent is subject to a terminal disclaimer.

(21) Appl. No.: 17/022,560

(22) Filed: Sep. 16, 2020

(65) Prior Publication Data

US 2020/0405738 A1   Dec. 31, 2020

Related U.S. Application Data

(63) Continuation of application No. 15/570,733, filed as application No. PCT/US2016/030391 on May 2, 2016, now Pat. No. 11,000,536.

(60) Provisional application No. 62/155,459, filed on Apr. 30, 2015.

(51) Int. Cl.

| | | |
|---|---|---|
| A61K 31/7036 | (2006.01) |
| A61K 31/05 | (2006.01) |
| A61K 31/19 | (2006.01) |
| A61K 31/203 | (2006.01) |
| A61K 31/352 | (2006.01) |
| A61K 31/4035 | (2006.01) |
| A61K 31/4164 | (2006.01) |
| A61K 31/4166 | (2006.01) |
| A61K 31/454 | (2006.01) |
| A61K 31/513 | (2006.01) |
| A61K 31/519 | (2006.01) |
| A61K 31/573 | (2006.01) |
| A61K 31/65 | (2006.01) |
| A61K 31/706 | (2006.01) |
| A61K 45/06 | (2006.01) |
| G01N 33/574 | (2006.01) |

(52) U.S. Cl.
CPC .......... *A61K 31/7036* (2013.01); *A61K 31/05* (2013.01); *A61K 31/19* (2013.01); *A61K 31/203* (2013.01); *A61K 31/352* (2013.01); *A61K 31/4035* (2013.01); *A61K 31/4164* (2013.01); *A61K 31/4166* (2013.01); *A61K 31/454* (2013.01); *A61K 31/513* (2013.01); *A61K 31/519* (2013.01); *A61K 31/573* (2013.01); *A61K 31/65* (2013.01); *A61K 31/706* (2013.01); *A61K 45/06* (2013.01); *G01N 33/574* (2013.01); *G01N 33/57488* (2013.01); *G01N 2800/52* (2013.01)

(58) Field of Classification Search
CPC ..... A61K 2300/00; A61K 45/06; A61P 35/00; A61P 35/02; A61P 35/04
See application file for complete search history.

(56) References Cited

U.S. PATENT DOCUMENTS

| | | | |
|---|---|---|---|
| 2006/0019256 A1 | 1/2006 | Clarke et al. |
| 2012/0058082 A1* | 3/2012 | Kaplan | A61P 29/00 424/85.5 |
| 2014/0088099 A1 | 3/2014 | Ren et al. |
| 2018/0289731 A1 | 10/2018 | Soon-Shiong |

FOREIGN PATENT DOCUMENTS

| | | |
|---|---|---|
| CA | 2 580 645 A1 | 3/2006 |
| CN | 1852974 A | 10/2006 |
| EP | 2 561 874 A2 | 2/2013 |
| JP | 2007-516693 A | 6/2007 |
| WO | 2005/005601 A2 | 1/2005 |
| WO | 2006/030473 A1 | 3/2006 |
| WO | 2009/012357 A2 | 1/2009 |
| WO | 2011/022440 A2 | 2/2011 |
| WO | 2012/151413 A1 | 11/2012 |
| WO | 2014/033322 A1 | 3/2014 |
| WO | 2014/062978 A1 | 4/2014 |

OTHER PUBLICATIONS

Xu et al (Cancer Immunol Immunother, 2013, vol. 62, pp. 1637-1648). (Year: 2013).*
Wang et al (Clinical Exp Metastasis, e-pub Jan. 25, 2015, vol. 32, pp. 111-124) (Year: 2015).*
Garcia et al (Urologic Oncology, 2014, vol. 32, pp. 33e11-33e17). (Year: 2014).*
Bhatnagar et al, Blood, 2010, vol. 116, pp. 1308-1316 (Year: 2010).*
Decision of Refusal received for Japanese Patent Application Serial No. 2017556861 dated Oct. 20, 2020, 2 pages (Including English Translation).
Final Office Action received for U.S. Appl. No. 15/570,733 dated Dec. 24, 2020, 18 pages.
Notice of Allowance received for U.S. Appl. No. 15/570,733 dated Mar. 25, 2021, 25 pages.
International Search Report and Written Opinion received for International PCT Application Serial No. PCT/US2016/030391, Oct. 19, 2016, 13 pages.

(Continued)

*Primary Examiner* — Karen A. Canella
(74) *Attorney, Agent, or Firm* — Martin Fessenmaier; Umberg Zipser LLP

(57) ABSTRACT

Compositions and methods for treatment of a condition associated with disease stem cells, and especially cancer stem cells are disclosed. In one aspect, a patient is treated with a stem cell differentiating agent and/or teratogenic pharmaceutical compound to induce one or more destructive pathways in the disease stem cells. Most typically, the destructive pathways include apoptotic pathways, necrotic pathways, and autophagy pathways.

11 Claims, No Drawings

(56) References Cited

OTHER PUBLICATIONS

Beckers et al., "Methotrexate enhances the antianabolic and antiproliferative effects of 5-aminoimidazole-4-carboxamide riboside," Molecular Cancer Therapeutics, Sep. 1, 2006, vol. 5, No. 9, pp. 2211-2217.
Cheng et al., "Methotrexate and 5-aminoimidazole-4-carboxamide riboside exert synergistic anticancer action against human breast cancer and hepatocellular carcinoma," Acta Pharmacologica Sinica, published online Apr. 22, 2013, vol. 34, pp. 951-959.
Non Final Office Action received for U.S. Appl. No. 15/570,733 dated Oct. 3, 2019, 23 pages.
Ha et al., "Mullerian inhibiting substance inhibits ovarian cell growth through an Rb-independent mechanism", Journal of Biological Chemistry, 2000, vol. 275, pp. 37101-37109.
Al-Khalaf et al., "p16INK4A enhances the transcriptional and the apoptotic functions of p53 through DNA-dependent interaction", Molecular Carcinogenesis, 2017, vol. 56, pp. 1687-1782.
Beck and Lloyd, Nature, 1964, vol. 201, pp. 1136-1137.
Examiner's Report received for Canadian Patent Application Serial No. 2990861 dated Jun. 20, 2019, 6 pages.
Pfeiffer et al., "Steroidogenic Enzymes and Stem Cell Markers Are Upregulated during Androgen Deprivation in Prostate Cancer", Molecular Medicine, 2011, vol. 17, No. 7-8, pp. 657-664.
Simmons et al., "NOTCH1 inhibition in vivo results in mammary tumor regression and reduced mammary tumorsphere-forming activity in vitro", Breast Cancer Research, vol. 14, No. 5, 2012, pp. 1-17.
Toor et al., "Epigenetic induction of adaptive immune response in multiple myeloma: sequential azacitidine and enalidomide generate cancer testis antigen-specific cellular immunity", British Journal of Haematology, 2012, vol. 158, No. 6, pp. 700-711.
Final Office Action received for U.S. Appl. No. 15/570,733 dated Apr. 17, 2020, 33 pages.
Testa et al., "CD 123 is a membrane biomarker and atherapeutic target in hematologic malignancies", Biomarker Research, 2014, vol. 2, No. 4, 11 pages.
Gupta et al., "Identification of Selective Inhibitorsof Cancer Stem Cells by High-Throughput Screening", Cell, 2009, vol. 138, pp. 645-659.
Prieto-Garcia et al., "Epithelial-to-mesenchymal transition in tumor progression", Medical Oncology, 2017, vol. 34, No. 122, 10 pages.
Huang et al., "Ovarian cancer stem cell-specific gene expression profiling and targeted drug prescreening", Oncology Reports, 2014, vol. 31, pp. 1235-1248.
Finones et al., "Early Human Prostate Adenocarcinomas Harbor Androgen-Independent Cancer Cells", Plos One, 2013, vol. 8, No. 9, 9 pages.
Office Action received for Canadian Patent Application Serial No. 2990861 dated Feb. 20, 2020, 6 pages.
Yoo et al., "A High-Content Assay to Identify SmallMolecule Modulators of a Cancer Stem Cell Population in Luminal Breast Cancer", Journal of Biomolecular Screening, 2012, vol. 17, No. 9, pp. 1211-1220.
Brown et al., "Morphoproteomic and pharmacoproteomic correlates in hormone-receptor-negative breast carcinoma Cell lines", Annals of Clinical & Laboratory Science, 2004, vol. 34, No. 3, pp. 251-262.
Shirsath et al., "Potentiation of anticancer effect of valproic acid, an antiepileptic agent with histone deacetylase Inhibitory activity, by the cyclin-dependent kinase inhibitor P276-00 in human non-small-cell lung cancer cell lines", Lung Cancer, 2013, vol. 82, pp. 214-221.
Naujokat et al., "Salinomycin as a Drug for Targeting Human Cancer Stem Cells", Journal of Biomedicine and Biotechnology, 2012, pp. 1-17.

Badros et al., "Phase I Trial of First-Line Bortezomib/Thalidomide plus Chemotherapy for Induction and Stem Cell Mobilization in Patients with Multiple Myeloma", Clinical Lymphoma & Myeloma, Nov. 2006, vol. 7, No. 3, pp. 210-216.
Verhelle et al., "Lenalidomide and CC-4047 Inhibit the Proliferation of Malignant B Cells while Expanding Normal CD34 + Progenitor Cells", Cancer Research, Jan. 15, 2007, vol. 67, No. 2, pp. 746-755.
First office action received for Chinese Patent Application Serial No. 201680039086.6 dated Apr. 3, 2020, 17 pages (Including English Translation).
Mian-fu et al., "Strategies of targeting cancer stem cell to treat malignant tumors", J Med Postgra, Aug. 2012, vol. J5, No. 8, pp. 886-888.
Notice of Reasons for Refusal received for Japanese Patent Application Serial No. JP2017-556861 dated Mar. 24, 2020, 8 pages (Including English Translation).
International Preliminary Report on Patentability Chapter II received for PCT Application Serial No. PCT/US2016/030391 dated Aug. 20, 2017, 17 pages.
Examination report received for Australian Patent Application Serial No. 2016255577 dated May 16, 2019, 4 pages.
Examination report received for Australian Patent Application Serial No. 2016255577 dated Nov. 22, 2019, 4 pages.
Figg et al., "A Randomized Phase II Trial of Thalidomide, an Angiogenesis Inhibitor, in Patients with Androgen-independent Prostate Cancer", Clinical Cancer Research, Jul. 2001, vol. 7, pp. 1888-1893.
Non Final Office Action received for U.S. Appl. No. 15/570,733 dated Aug. 26, 2020, 30 pages.
Ramachandran et al., "Concise Review: the Coming of Age of Stem Cell Treatment for Corneal Surface Damage", Stem Cells Translational Medicine, 2014, vol. 3, pp. 1160-1168.
Segers., "Stem-cell therapy for cardiac disease", Nature, 2008, vol. 451, pp. 937-942.
Lunn et al., "Stem Cell Technology for Neurodegenerative Diseases", Annuals of Neurology, 2011, vol. 70, pp. 353-361.
Kuo et al., "Stem Cell Therapy for Liver Disease: Parameters Governing the Success of Using Bone Marrow Mesenchymal Stem Cells", Gastroenterology, 2008, vol. 134, pp. 2111-2121.
Pang et al., "Hematopoietic stem cell and progenitor cell mechanisms in myelodysplastic syndromes", PNAS, 2013, vol. 110, pp. 3011-3016.
Marx Vivien, "A dream of single-cell proteomicsA dream of single-cell proteomics", Nature Methods, 2019, vol. 16, pp. 809-812.
Budnik et al., "SCoPE-MS: mass spectrometry of single mammalian cells quantifies proteome heterogeneity during cell differentiation", Genome Biology, 2018, vol. 19, No. 161, 12 pages.
Knox et al., "Modeling luminal breast cancer heterogeneity: combination therapy to suppress a hormone receptor-negative, cytokeratin 5-positivesubpopulation in luminal disease", Breast Cancer Research, 2014, vol. 16, 13 pages.
Bartholoma et al., "A More Aggressive Breast Cancer Spheroid Model Coupled to an Electronic Capillary Sensor System for a High-Content Screening of Cytotoxic Agents in Cancer Therapy: 3-Dimensional In Vitro Tumor Spheroids as a Screening Model" Journal of Biomolecular Screening, 2005, vol. 10, pp. 705-714.
Horwitz et al., "Rare steroid receptor-negative basal-like tumorigenic cells in luminal subtype human breast cancer xenografts", PNAS, 2008, vol. 105, pp. 5774-5779.
Notice of Allowance received for U.S. Appl. No. 15/570,733 dated Jun. 17, 2020, 22 pages.
Notice of Being Deemed to have been withdrawn received for Chinese Patent Application Serial No. 2016800390866 dated dated Sep. 24, 2020, 2 pages (Including English Translation).

* cited by examiner

PATIENT TREATMENT VIA TERATOGENIC PHARMACEUTICAL COMPOUNDS

This application is a continuation application of US application with the Ser. No. 15/570,733, filed Oct. 30, 2017, and which is a 371 application of PCT/US2016/030391, filed May 2, 2016, and which claims priority to US provisional application with the Ser. No. 62/155459, filed Apr. 30, 2015.

FIELD OF THE INVENTION

The field of the invention is use of pharmaceutical compounds that induce changes in differentiation or cell cycle, and especially teratogenic agents and differentiating agents for treatment of neoplastic diseases associated with cancer stem cells.

BACKGROUND OF THE INVENTION

The background description includes information that may be useful in understanding the present inventive subject matter. It is not an admission that any of the information provided herein is prior art or relevant to the presently claimed inventive subject matter, or that any publication specifically or implicitly referenced is prior art.

Billions of dollars are spent annually on research and development of new cancer drugs or treatments. Typically such R&D covers broad spectrum of development activities including identification of new chemical entities, determining viability of such entities, testing for toxicity, animal testing, creating formulations, scaling production, seeking regulatory approval, and more. Beyond the outlay of money, in practice, a company could easily spend 10 or more years in developing a new compound of use in the market. At any point along the complex R&D path, the new compound might result in a dead end. Even in view of the high risks and costs associated with drug development, the return on investment could be quite high if a market-viable compound is found. However, the loss of the investment could be quite high should the results be a dead end.

In many cases, the development of a new drug is abandoned or simply not pursued because the drug fails one or more regulatory requirements. Consider, for example, a new compound that has been found to be teratogenic. Such a drug would not be pursued because it might cause birth defects. In fact, significant effort has been applied toward determining if a compound is teratogenic, as can be seen from US 2015/0133340 or WO 2014/071137. All patent applications and publications identified herein are incorporated by reference to the same extent as if each individual patent application or publication were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Similarly, certain differentiation agents have been reported as being successful treatment modalities for an already existing malignant cell. For example, all-trans retinoic acid was shown to be effective in many cases of acute promyelocytic leukemia to push promyelocytic cells in to downstream maturity and so reduce or even eliminate cancerous population growth (*Oncogene* 2001; 20, 7140-7145). However, such treatment is limited to specific lineage committed cells and thus not contemplated for other types of malignancies.

Next to differentiation agents, thalidomide was reported as an angiogenesis inhibitor in androgen-independent prostate cancer when administered at low dose of 200 mg/d (*Clin Cancer Res.* 2001) while inconclusive results were reported for thalidomide in non-small cell lung cancer (*Contemp Oncol* (Pozn). 2014; 18(1): 39-47). In yet another report thalidomide plus radiation was shown to reduce VEGF levels in esophageal cancer patients (*World J Gastroenterol* 2014 May 7; 20(17): 5098-103), leading the authors to speculate that treatment outcome may improve using thalidomide in such malignancy. In addition, immune modulating effects were also proposed as mechanism for thalidomide in the treatment of multiple myeloma (*Science* 2014 Jan. 17; 343(6168): 256-257; PLoS One. 2013 May 14; 8(5): e64354). However, despite these limited mechanistic insights, these observed effects have not led to effective cancer treatment.

Therefore, even though various compositions and methods for cell treatment are known in the art, all or almost all of them suffer from one or more disadvantages. Therefore, there is still a need for improved pharmaceutical intervention for malignant diseases, and especially malignant diseases cause by cancer stem cells.

SUMMARY OF THE INVENTION

The inventive subject matter is directed to compounds, compositions, and methods in which a differentiating agent and/or teratogenic pharmaceutical compound is used for cancer treatment, and especially treatment and prevention of cancers originating from cancer stem cells. Most typically, thusly treated cells will activate a destructive pathway in cancer stem cells.

In one aspect of the inventive subject matter, the inventors contemplate a method of treating a diseased tissue that includes a step of determining from a sample taken from the diseased tissue that a disease stem cell is present in the sample, wherein the disease stem cell has at least one stem cell attribute and at least one differentiated cell attribute. Contemplated methods will also include a further step of administering an effective amount of a teratogenic pharmaceutical compound and/or stem cell differentiating agent to the diseased tissue to so activate a destructive pathway (e.g., an apoptosis pathway or an autophagy pathway) in disease stem cells remaining in the diseased tissue. Most typically such activation may proceed via activation of a Fas receptor, TNFR1 (Tumor Necrosis Factor Receptor-1), an Apo2 receptor, an Apo3 receptor, a caspase, a ZIP kinase, Bc12, BAX, p53, and/or SMAC (Second Mitochondria-Derived Activator of Caspase)

Typically, the diseased tissue comprises a neoplastic tissue, and most typically a cancerous tissue (e.g., breast cancer tissue, colon cancer tissue, prostate cancer tissue, glioblastoma tissue, ovarian cancer tissue, head and neck cancerous tissue, melanoma tissue, basal cell cancer, squamous cell cancer, gastric cancer tissue, pancreatic cancer tissue, or lung cancer tissue). While not limiting the inventive subject matter, it is generally preferred that the step of determining comprises transcriptomics analysis, proteomics analysis, mass spectroscopy analysis, and/or immunohistochemical analysis of at least a portion of the diseased tissue. Depending on the particular tissue, the stem cell attribute may be CD19, CD24, CD34, CD44, CD90 (Thy1), CD117, CD133, CD200 (OX-2), EpCAM (epithelial cell adhesion molecule), and/or ABCB5 (ATP-binding cassette B5), while the differentiated cell attribute may include Fox3, MAP2, beta III tubulin, BRCA1, cytokeratin 5, podocalyxin, cytokeratin 8, cytokeratin 14, cytokeratin 18, MUC-1, CA125, cytokeratin 18, HSP27, cytokeratin 15, CD138, cornulin, cathepsin E, desmocollin-2, caveolin-1, foxa1, and/or Rex-1.

Among other suitable choices, contemplated teratogenic pharmaceutical compounds include an ACE (angiotensin converting enzyme), an androgen, isotretinoin, a tetracycline, a doxycycline, a streptomycin, phenytoin, valproic acid, methotrexate, aminopterin, a thiouracil, a carbimazole, DES, thalidomide, lenalidomide, pomalidomide, and apremilast. Contemplated stem cell differentiating agents include AICAR (N1-(β-D-Ribofuranosyl)-5-aminoimidazole-4-carboxamide), 5-azacytidine, CCG1423 (N-[2-[(4-Chlorophenyl)amino]-1-methyl-2-oxoethoxy]-3,5-bis(trifluoromethyl)benzamide), CW 008 (4-Fluoro-N-[5-fluoro-6-(5-methoxypyrazolo[1,5-a]pyridin-3-yl)-1H-pyrazolo[3,4-b]pyridin-3-yl]benzamide), cyclopamine, DAPT (N-[(3,5-Difluorophenyl)acetyl]-L-alanyl-2-phenyl]glycine-1,1-dimethylethyl ester), dexamethasone, forskolin, retinoic acid, and SIS3 (1,2,3,4-Tetrahydro-6,7-dimethoxy-2-[(2E)-3-(1-phenyl-1H-pyrrolo[2,3-b]pyridin-3-yl)-1-oxo-2-propenyl]-soquinoline hydrochloride).

Additionally, it is generally preferred that the teratogenic pharmaceutical compound and/or stem cell differentiating agent is administered to the diseased tissue in vivo. For example, where the teratogenic pharmaceutical compound and/or stem cell differentiating agent is a prescription drug, it may be administered to the diseased tissue in an amount of less than 50%, or less than 25%, or even less than 10% (but above 0.1%) of an otherwise recommended prescription dosage. Additionally, or alternatively, the teratogenic pharmaceutical compound and/or stem cell differentiating agent may also be metronomically administered, typically in an amount below a prescription dosage.

Viewed form a different perspective, the inventors therefore also contemplate a method of reducing a number of cancer stem cells in a patient. Particularly contemplated methods will include a step of determining from a sample taken from a cancer tissue of the patient that a cancer stem cell is present in the sample, wherein the cancer stem cell has at least one stem cell attribute and at least one differentiated cell attribute; and another step of administering an effective amount of a teratogenic pharmaceutical compound and/or stem cell differentiating agent to the patient to so reduce the number of cancer stem cells by activating a destructive pathway in cancer stem cells remaining in the patient.

As noted above, contemplated cancer tissues include a breast cancer tissue, a colon cancer tissue, a prostate cancer tissue, a glioblastoma tissue, an ovarian cancer tissue, a head and neck cancerous tissue, a melanoma tissue, a basal cell cancer, a squamous cell cancer, a gastric cancer tissue, a pancreatic cancer tissue, and a lung cancer tissue, while the step of determining may comprise at least one of transcriptomics analysis, proteomics analysis, mass spectroscopy analysis, and immunohistochemical analysis. With respect to the stem cell attribute, the differentiated cell attribute, the teratogenic pharmaceutical compound, and the stem cell differentiating agent, and administration, the same considerations as provided above apply.

Consequently, the inventors also contemplate use of a teratogenic pharmaceutical compound and/or stem cell differentiating agent to activate a destructive pathway in a disease stem cell wherein the disease stem cell has at least one stem cell attribute and at least one differentiated cell attribute. As before, contemplated stem cell attributes include CD19, CD24, CD34, CD44, CD90 (Thy1), CD117, CD133, CD200 (OX-2), EpCAM (epithelial cell adhesion molecule), and ABCB5 (ATP-binding cassette B5), and it is further contemplated that the disease stem cell is from a breast cancer tissue, a colon cancer tissue, a prostate cancer tissue, a glioblastoma tissue, an ovarian cancer tissue, a head and neck cancerous tissue, a melanoma tissue, a basal cell cancer, a squamous cell cancer, a gastric cancer tissue, a pancreatic cancer tissue, or a lung cancer tissue.

Likewise, it is contemplated that is such uses the teratogenic pharmaceutical compound may be an ACE (angiotensin converting enzyme), an androgen, isotretinoin, a tetracycline, a doxycycline, a streptomycin, phenytoin, valproic acid, methotrexate, aminopterin, a thiouracil, a carbimazole, DES, thalidomide, lenalidomide, pomalidomide, and/or apremilast, while the stem cell differentiating agent may be AICAR (N1-(β-D-Ribofuranosyl)-5-aminoimidazole-4-carboxamide), 5-azacytidine, CCG1423 (N-[2-[(4-Chlorophenyl)amino]-1-methyl-2-oxoethoxy]-3,5-bis(trifluoromethyl)benzamide), CW 008 (4-Fluoro-N-[5-fluoro-6-(5-methoxypyrazolo[1,5-a]pyridin-3-yl)-1H-pyrazolo[3,4-b]pyridin-3-yl]benzamide), cyclopamine, DAPT (N-[(3,5-Difluorophenyl)acetyl]-L-alanyl-2-phenyl]glycine-1,1-dimethylethyl ester), dexamethasone, forskolin, retinoic acid, and/or SIS3 (1,2,3,4-Tetrahydro-6,7-dimethoxy-2-[(2E)-3-(1-phenyl-1H-pyrrolo[2,3-b]pyridin-3-yl)-1-oxo-2-propenyl]-isoquinoline hydrochloride).

Various objects, features, aspects and advantages of the inventive subject matter will become more apparent from the following detailed description of preferred embodiments.

DETAILED DESCRIPTION

To date, diseases such as cancer are treated only as a proliferation problem. Current treatments focus on stopping or halting proliferation. However, even after such treatments, cancer can return to the patient, even in circumstances where the patient appears to be in remission. Thus, a different perspective on cancer is required to address such issues.

It is thought that in order to have a significant impact on treating cancer, each individual type of cancer cell (e.g., cancer stem cell, cancer progenitor cell, cancer metastatic cell, etc.) must be attacked, possibly via different treatments. In the past, as alluded to above, these various types of cancer cells have been treated as a single type of proliferation problem. For example, chemotherapy is used to treat the cancer as a whole, but might only wipe out proliferated cancer cells and, unfortunately, healthy cells as well. However, in the cancer model discussed above, the chemotherapy would not necessarily rid the patient of the cancer stem cells. Thus, the cancer can return possibly in a differentiated form. Simply put, each type of cancer cell could require a different treatment strategy.

With respect to cancer stem cells, in situations where the cancer stem cells cannot be treated via chemotherapy or other traditional routes, the cancer stems cells can be attacked via their cellular metabolism governed by one or more signaling pathways.

The inventor has discovered that disease stem cells, and especially cancer stem cells can be treated with a teratogenic pharmaceutical compound and/or stem cell differentiating agent such that the disease/cancer stem cell activates a destructive pathway, which will then lead to activation of a destructive pathway, and especially activation of an apoptosis pathway or an autophagy pathway. Based on this observation, the inventor therefore contemplates a method of treating a diseased (typically neoplastic or cancerous)

tissue in which presence of a disease/cancer stem cell is first determined using omics or immunohistochemical methods well known in the art. Upon determination that a disease/cancer stem cell is present, an effective amount of a teratogenic pharmaceutical compound and/or stem cell differentiating agent is administered to the diseased tissue to so activate a destructive pathway in disease or cancer stem cells remaining in the diseased tissue.

Most typically, contemplated cancer stem cells will exhibit certain stem cell attributes and most commonly have one or more surface markers to stem cells and known cancer stem cells. For example, cancer stem cells may exhibit CD19, CD24, CD34, CD44, CD90 (Thy1), CD117, CD133, CD200 (OX-2), EpCAM (epithelial cell adhesion molecule), and/or ABCB5 (ATP-binding cassette B5). Of course, it should be noted that such markers can be selectively expressed in a particular cancer stem cell, and that different cancers will have different cancer stem cells with their respective surface markers. For example, contemplated cancer tissues in which the cancer stem cells reside include breast cancer tissue, colon cancer tissue, prostate cancer tissue, glioblastoma tissue, ovarian cancer tissue, head and neck cancerous tissue, basal cell cancer tissue, squamous cell cancer tissue, melanoma tissue, gastric cancer tissue, pancreatic cancer tissue, and lung cancer tissue. In that context, it should be appreciated that the cancer stem cells need not necessarily be located in the cancer mass, but may reside distal and/or in a dormant form. As such, and especially where cancer stem cells are quiescent, traditional chemotherapeutic agents will not be effective as most of these agents require cell division to be effective.

While it is generally contemplated that the disease/cancer stem cell is obtained from a sample or biopsy of a tumor, it should be appreciated that circulating tumor cells (CTC) may also be identified in a blood sample, where the CTCs could comprise one or more cancer stem cells. For example, CTCs could be enriched from the blood sample through be-bulking techniques, possibly based on those described in U.S. Pat. No. 8,569,009.

Analysis of the cancer stem cell will also involve a confirmation that the cancer stem cell has at least one differentiated cell attribute. For example, where the cancer is a neural cancer, contemplated attributes may include Fox3, MAP2, and/or beta III tubulin, or where the cancer is a breast cancer, the attribute may include BRCA1, cytokeratin 5, or podocalyxin. Similarly, where the cancer is prostate cancer, the attribute may be cytokeratin 8, 14, and/or 18 and where the cancer is ovarian cancer, the attribute may be MUC-1, CA125, or cytokeratin 18. Melanoma attributes include HSP27, while basal cell cancer attributes include cytokeratin 15 and squamous cell cancer attributes include CD138 and/or cornulin. In further examples, cathepsin E or desmocollin-2 may serve as an attribute for gastric cancer, while attributes for lung cancer include caveolin-1, foxa1, and Rex-1.

For confirmation of the presence of the stem cell and differentiated cell attributes it is contemplated that all manners are deemed suitable. Most typically, as the attributes need to be expressed, contemplated analytical methods especially include methods that directly or indirectly confirm the presence or absence of the markers. Therefore, among other suitable methods, immunohistochemical tests using labeled antibodies on tissue sections (fixed or fresh) are deemed appropriate. Alternatively, qualitative and quantitative mass spectroscopic methods or proteomics methods (e.g., using gel electrophoresis or mass spec immune assay) are also contemplated. Furthermore, indirect confirmation methods that indicate marker expression include transcriptomic analyses, and especially qualitative and quantitative transcriptomic analyses (e.g., using qPCR, micro arrays, or whole transcriptome shotgun sequencing).

Therefore, with respect to identification of the disease/cancer stem cell it should be noted that all manners of identification or detection are deemed suitable for use herein, and that the most appropriate manner of detection or identification will typically depend to at least some degree of the desired marker used for the disease/cancer stem cell. However, in most contemplated methods, a sample is obtained from the diseased or cancerous tissue and the presence of the disease/cancer stem cell is determined following methods as noted above. Once confirmed that the disease/cancerous tissue comprises a disease/cancer stem cell, the tissue can then be exposed to one or more teratogenic pharmaceutical compound and/or stem cell differentiating agent. Of course, it should be recognized that such exposure can be performed in vitro or in vivo. Consequently, the manner of administering the teratogenic pharmaceutical compound and/or stem cell differentiating agent may vary considerably.

For example, where the diseased/cancerous tissue is contacted with the teratogenic pharmaceutical compound and/or stem cell differentiating agent in vitro, contacting may be performed in cell or tissue culture, typically by combining the teratogenic pharmaceutical compound and/or stem cell differentiating agent with a culture or incubation medium at a suitable concentration. As will be readily appreciated, the appropriate concentration can be ascertained using one or more test procedures that establish that a destructive pathway has been activated in the disease/cancer stem cells as further described in more detail below. On the other hand, where the teratogenic pharmaceutical compound and/or stem cell differentiating agent is administered in vivo, contacting may be performed using all known manners of administering a pharmaceutical compound to a patient, especially via oral or parenteral administration (e.g., intravenous injection, intramuscular injection, inhalation, etc.). Advantageously, as numerous teratogenic pharmaceutical compounds and stem cell differentiating agents are known in the art, administration in vivo may follow the same route, dosage, and schedule as is noted for such compounds and agents (typically set forth in the prescribing information).

The inventor has now appreciated that, although use of such compounds and/or agents could be problematic in some contexts (e.g., during pregnancy), especially over an extended period and at relatively high dosages, low dose administration of such compounds and agents may advantageously achieve the same effect on cancer stem cells without triggering adverse effects (or with a reduced frequency) otherwise observed. Therefore, the inventor contemplates that the teratogenic pharmaceutical compound and/or stem cell differentiating agent is administered to the diseased tissue in an amount of less than 50% of a prescription dosage, and more preferably less than 25% of a prescription dosage, and most preferably less than 10% of a prescription dosage. Moreover, to sustain the desired effect of activating a destructive pathway in the disease/cancer stem cells it is contemplated that the teratogenic pharmaceutical compound and/or stem cell differentiating agent is administered at a reduced dosage (as compared to prescribing information) in a metronomic fashion. For example, the compound or drug may be administered orally at 20% of a dosage indicated in the prescribing information over a period of 2 months every 4 days. Thus, metronomic administration will advantageously extend over at least two weeks, and more preferably over at least four weeks, and most preferably over at least 8 weeks at dosage levels between 1-10%, or between 10-25%, or between 25-50% of the indicated dosage in the prescribing information. Such metronomic low dose administration is thought to maintain activation of the destructive pathway in the disease/cancer stem cells without significantly producing adverse effects in non-disease/cancer stem cells.

With respect to suitable teratogenic pharmaceutical compounds it should be noted that all pharmaceutical agents with teratogenic activity are deemed appropriate for use herein, and that teratogenic activity is either known for such agents or can be ascertained following protocols well know in the art (see e.g., US 2015/0133340A1 or WO 2014/071137A1). For example, suitable teratogenic agents include various an ACE (angiotensin converting enzyme) inhibitors such as benazepril, captopril, enalapril, fosinopril sodium, lisinopril, lisinopril, hydrochlorothiazide, quinapril, and ramipril, certain androgens (and especially testosterone derivatives), diethylstilbestrol, isotretinoin, certain antibiotics (e.g., tetracycline, doxycycline, streptomycin), certain anticonvulsants such as phenytoin, valproic acid, trimethadione, paramethadione, and carbamazepine, and methotrexate, aminopterin, thiouracil, carbimazole, thalidomide, lenalidomide, pomalidomide, and apremilast.

Similarly, there are numerous the stem cell differentiating agents known in the art, and especially contemplated agents include those that induce endoderm formation, ectoderm formation, mesoderm formation, and those that facilitate neuronal differentiation, osteoblast or adipocyte formation, cardiomyogenic differentiation, etc. Therefore, exemplary stem cell differentiating agents suitable for use herein include AICAR ($N^1$-(β-D-Ribofuranosyl)-5-aminoimidazole-4-carboxamide), 5-azacytidine, CCG1423 (N-[2-[(4-Chlorophenyl)amino]-1-methyl-2-oxoethoxy]-3,5-bis(trifluoromethyl)benzamide), CW 008 (4-Fluoro-N-[5-fluoro-6-(5-methoxypyrazolo[1,5-a]pyridin-3-yl)-1H-pyrazolo[3,4-b]pyridin-3-yl]benzamide), cyclopamine, DAPT (N-[(3,5-Difluorophenyl)acetyl]-L-alanyl-2-phenyl]glycine-1,1-dimethylethyl ester), dexamethasone, forskolin, retinoic acid, and SIS3 (1,2,3,4-Tetrahydro-6,7-dimethoxy-2-[(2E)-3-(1-phenyl-1H-pyrrolo[2,3-b]pyridin-3-yl)-1-oxo-2-propenyl]-isoquinoline hydrochloride). Further suitable compounds and compositions known to induce differentiation of a stem cell into any one of the three germ layer cell types include those described in "Reviews in Stem and Progenitor Cells" (*The Scientific World Journal* (2002) 2, 1147-1166). Suitable agents also include those that trans-differentiate an at least lineage-committed cell to another lineage or type without passing through a stem cell type stage (see e.g., *Mol Hum Reprod Volume* 16, Issue 11; Pp. 856-868; or *Mol Hum Reprod* 2010 Nov; 16(11): 856-68).

Depending on the particular teratogenic pharmaceutical compound and/or stem cell differentiating agent it should be appreciated that the particular mechanism of action may vary to at least some degree. However, it is generally contemplated that the compounds and agents contemplated herein will trigger or activate an apoptosis pathway and/or an autophagy pathway. Viewed from another perspective, the teratogenic pharmaceutical compound and/or stem cell differentiating agent may interfere with one or more components present in Wnt/β-catenin signaling, in Hippo signaling, in Notch signaling, in Hedgehog signaling, in TGF-β signaling, and/or in G-protein signaling. Therefore, it should be appreciated that destructive pathways may be activated by a Fas receptor or ligand thereof, TNFR1 (Tumor Necrosis Factor Receptor-1) or ligand thereof, an Apo2 receptor or ligand thereof, an Apo3 receptor or ligand thereof, a caspase, a SMAC (Second Mitochondria-Derived Activator of Caspase), a ZIP kinase, Bcl2, BAX, and/or p53.

Regardless of the particular compound or agent, it should thus be appreciated that the disease/cancer stem cell will undergo an event that, even at low concentrations, will dispose the disease/cancer stem cell towards activation of a destructive pathway that will ultimately lead to a breakdown of the disease/cancer stem cell. Moreover, as the disease/cancer stem cell undergoes apoptosis or autophagy, numerous proteins and protein fragments are released that may in turn serve as a triggering event for the immune system to recognize and target a response against the dying disease/cancer stem cell. Notably, as all or almost all of the disease/cancer stem cell will express neoepitopes due to mutations, such neoepitopes may become antigens against which the immune system can mount a therapeutically effective response.

In addition, it is contemplated that a secondary drug may be provided to the cancer or patient to augment or synergistically enhance activation of the destructive pathway. Most preferably, secondary drugs include all known chemotherapeutic drug, particularly where such drugs are (co-) administered in a low dose metronomic regimen as described above.

Therefore, contemplated composition and methods may also be useful to reduce the number of cancer stem cells in a patient. To that end, it is generally contemplated that first a sample is taken from the cancer tissue, and that the cancer tissue contains a cancer stem cell. As noted before, suitable cancer stem cells will have at least one stem cell attribute and at least one differentiated cell attribute. Upon confirmation of the presence of a cancer stem cell, an effective amount of a teratogenic pharmaceutical compound and/or stem cell differentiating agent is administered to the patient to so reduce the number of cancer stem cells by activating a destructive pathway in cancer stem cells remaining in the patient. Thus, viewed from a different perspective, the inventors also contemplate the use of a teratogenic pharmaceutical compound and/or stem cell differentiating agent to activate a destructive pathway in a disease stem cell (wherein the disease stem cell has at least one stem cell attribute and at least one differentiated cell attribute). With respect to the cancer stem cell, the attributes, the teratogenic pharmaceutical compound and/or stem cell differentiating agent, and the administration, the same considerations as provided above apply.

It should still further be appreciated that somatic cells proliferate through standard mitosis, at least up to a Hayflick limit. Stem cells, on the other hand, do not necessarily follow the same processes as somatic cells; for example stem cells are able to self-renew. Rather, stem cells can self-renew through routes such a symmetric cell division, asymmetric cell division (e.g., intrinsic, extrinsic, etc.), or other routes unavailable to somatic cells that are fully differentiated. As a more specific example, consider totipotent zygote cells. In zygote growth the cells divide via cell cleavage. Before the 8-cell phase, each cell remains substantially unspecialized and could individually become separate organisms where each cell can be considered a stem cell. One of the significant differences between stem cells and somatic cells is that the stem cells can be considered immortal based on high telomerase activity that allow renewal of the stem cell's telomeres, which prevents telomere triggered apoptosis.

Cancer stem cells are thought to following similar self-renew routes as standard stem cells. Consequently, cancer stem cells could self-renew through similar stem cell renewal routes, chemotherapy or other cancer treatments that target proliferated, differentiated cancer cells would be unable to target the cancer stem cells in a significant way. The Applicants have appreciated that targeting the specialized cell division or self-renewal routes of the cancer stem cells with drugs, molecules, or other pharmaceutical compounds offers additional paths to treating a patient where traditional treatments such as chemotherapy have failed. Thus, the inventive subject matter is also considered to include development of or use of teratogenic pharmaceutical compounds, stem cell differentiating agents, or other compounds, that specifically attack the specialized cancer stem cell routes of self-renewal or cell division.

Yet another aspect of the inventive subject matter includes use of pharmaceutical compounds that break cancer cell tolerance of NK cells or that possibly make cancer stem cells visible to NK cells so that the NK cells are able to trigger apoptosis pathways. In such embodiments, the NK cells' cytotoxicity can be considered reactivated with respect to the target cells (e.g., cancer progenitor cell, cancer tumor cell, cancer stem cell, etc.). The NK cells can have their cytotoxicity activated through cytokines or compounds that operate as cytokines.

In some embodiments, combinations of one or more compounds or molecules can operate to increase the cytotoxicity of NK cells when proximal to target cancer cells. Example compounds or analogs thereof include COX-2 inhibitors, metformin, granulocyte macrophage colony-stimulating factor (GM-CSF), and granulocyte colony-stimulating factor (GCSF) to name a few. Such compounds, alone or combined, can impact how cytokines active NK cells relative to the target cancer cells.

Further, in some embodiments, compounds such as GCSF or interferon are thought to induce cancer stem cells to become cancer progenitor cells. The cancer progenitor cells can then divided normally. Thus, the cancer stem cells, which would normally not be affected by chemotherapy, can be caused to become susceptible to chemotherapy due to becoming differentiated. This strategy combined with the previously discussed strategies offers multiple paths through which a patient can be treated for cancer, especially cancers that are associated with cancer stem cells.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification or claims refer to at least one of something selected from the group consisting of A, B, C . . . and N, the text should be interpreted as requiring only one element from the group, not A plus N, or B plus N, etc.

What is claimed is:

1. A method of breaking tolerance of an NK cell to a cancer cell, the method comprising:
   administering an effective amount of a teratogenic pharmaceutical compound and/or stem cell differentiating agent to the cancer cell to activate a destructive pathway in the cancer cell; and
   increasing cytotoxicity of NK cells by administering at least one of a COX-2 inhibitor, metformin, and granulocyte colony-stimulating factor (GCSF).

2. The method of claim 1, wherein the cancer cell is a cancer stem cell.

3. The method of claim 1, wherein the teratogenic pharmaceutical compound and/or stem cell differentiating agent is administered to the cancer cell in vitro.

4. The method of claim 1, wherein the teratogenic pharmaceutical compound and/or stem cell differentiating agent is administered in a metronomic fashion.

5. The method of claim 1, wherein the cancer cell is from a cancerous tissue and wherein the cancerous tissue is a breast cancer tissue, a colon cancer tissue, a prostate cancer tissue, a glioblastoma tissue, an ovarian cancer tissue, a head and neck cancerous tissue, a melanoma tissue, a basal cell cancer, a squamous cell cancer, a gastric cancer tissue, a pancreatic cancer tissue, or a lung cancer tissue.

6. The method of claim 1, wherein the teratogenic pharmaceutical compound is selected from the group consisting of an ACE (angiotensin converting enzyme) inhibitors, an androgen, isotretinoin, a tetracycline, a doxycycline, a streptomycin, phenytoin, valproic acid, methotrexate, aminopterin, a thiouracil, a carbimazole, DES, thalidomide, lenalidomide, pomalidomide, and apremilast.

7. A method of rendering a cancer cell visible to an NK cell, the method comprising:
   administering an effective amount of a teratogenic pharmaceutical compound and/or stem cell differentiating agent to the cancer cell to activate a destructive pathway in the cancer cell; and
   increasing cytotoxicity of NK cells by administering at least one of a COX-2 inhibitor, metformin, and granulocyte colony-stimulating factor (GCSF).

8. The method of claim 7, wherein the teratogenic pharmaceutical compound and/or stem cell differentiating agent is administered to the cancer cell in vitro.

9. The method of claim 7, wherein administration of the teratogenic pharmaceutical compound and/or stem cell differentiating agent is performed in a metronomic fashion.

10. The method of claim 7, wherein the cancer cell is from a cancerous tissue and wherein the cancerous tissue is a breast cancer tissue, a colon cancer tissue, a prostate cancer tissue, a glioblastoma tissue, an ovarian cancer tissue, a head and neck cancerous tissue, a melanoma tissue, a basal cell cancer, a squamous cell cancer, a gastric cancer tissue, a pancreatic cancer tissue, or a lung cancer tissue.

11. The method of claim 7, wherein the teratogenic pharmaceutical compound is selected from the group consisting of an ACE (angiotensin converting enzyme) inhibitors, an androgen, isotretinoin, a tetracycline, a doxycycline, a streptomycin, phenytoin, valproic acid, methotrexate, aminopterin, a thiouracil, a carbimazole, DES, thalidomide, lenalidomide, pomalidomide, and apremilast.

* * * * *